United States Patent [19]
Daigle et al.

[11] Patent Number: 5,549,703
[45] Date of Patent: Aug. 27, 1996

[54] ORTHOPEDIC PROSTHESIS APPARATUS WITH IMPROVED TAPER LOCKING CONNECTION

[75] Inventors: Kenneth P. Daigle, Olive Branch, Miss.; Mark E. Harbaugh, Memphis, Tenn.

[73] Assignee: Smith & Nephew Richards Inc., Memphis, Tenn.

[21] Appl. No.: 389,914

[22] Filed: Feb. 16, 1995

[51] Int. Cl.⁶ .................................................. A61F 2/36
[52] U.S. Cl. ................................................ 623/23; 623/19
[58] Field of Search ...................... 623/18, 19, 20, 623/23; 403/375, 361, 345

[56] References Cited

U.S. PATENT DOCUMENTS

| | | | |
|---|---|---|---|
| 3,830,008 | 8/1974 | Johnson | 403/361 |
| 4,012,795 | 3/1977 | Doore et al. | 3/1.91 |
| 4,058,856 | 11/1977 | Doerre et al. | 3/1.19 |
| 4,170,794 | 10/1979 | Zeibig et al. | 3/1.91 |
| 4,198,711 | 4/1980 | Zeibig | 3/1.91 |
| 4,227,265 | 10/1980 | Frey | 403/361 |
| 4,268,919 | 5/1981 | Zeibig | 3/1.91 |
| 4,532,660 | 8/1985 | Field | 623/18 |
| 4,921,500 | 5/1990 | Averill et al. | 623/22 |
| 4,964,869 | 10/1990 | Auclair et al. | 623/23 |
| 5,080,685 | 1/1992 | Bolesky et al. | 623/23 |
| 5,108,452 | 4/1992 | Fallin | 623/23 |
| 5,112,156 | 5/1992 | Boyer | 403/287 |
| 5,122,141 | 6/1992 | Simpson et al. | 606/62 |
| 5,181,929 | 1/1993 | Prats et al. | 623/23 |
| 5,246,462 | 9/1993 | Bekki et al. | 623/23 |

FOREIGN PATENT DOCUMENTS

| | | | |
|---|---|---|---|
| 393608 | 10/1990 | European Pat. Off. | 623/23 |
| 660681 | 6/1987 | Switzerland | 623/23 |

OTHER PUBLICATIONS

Genesis™ Total Knee System, Smith & Nephew Richards.

*Primary Examiner*—Michael J. Milano
*Attorney, Agent, or Firm*—Pravel, Hewitt, Kimball & Krieger

[57] ABSTRACT

An orthopedic joint prosthesis includes a prosthesis body with a pair of connectable components each having a connecting portion with a generally frustroconically shaped surface. One of the components has a projecting connecting portion and the other component has a socket connecting portion. The projecting connecting portion has a distal end and a proximal end with a generally circular end face. The void space can also be a socket. The void space defines a means for distributing stress between the proximal and distal end portions after the prosthesis body has been assembled by locking the socket and projecting portions together.

8 Claims, 3 Drawing Sheets

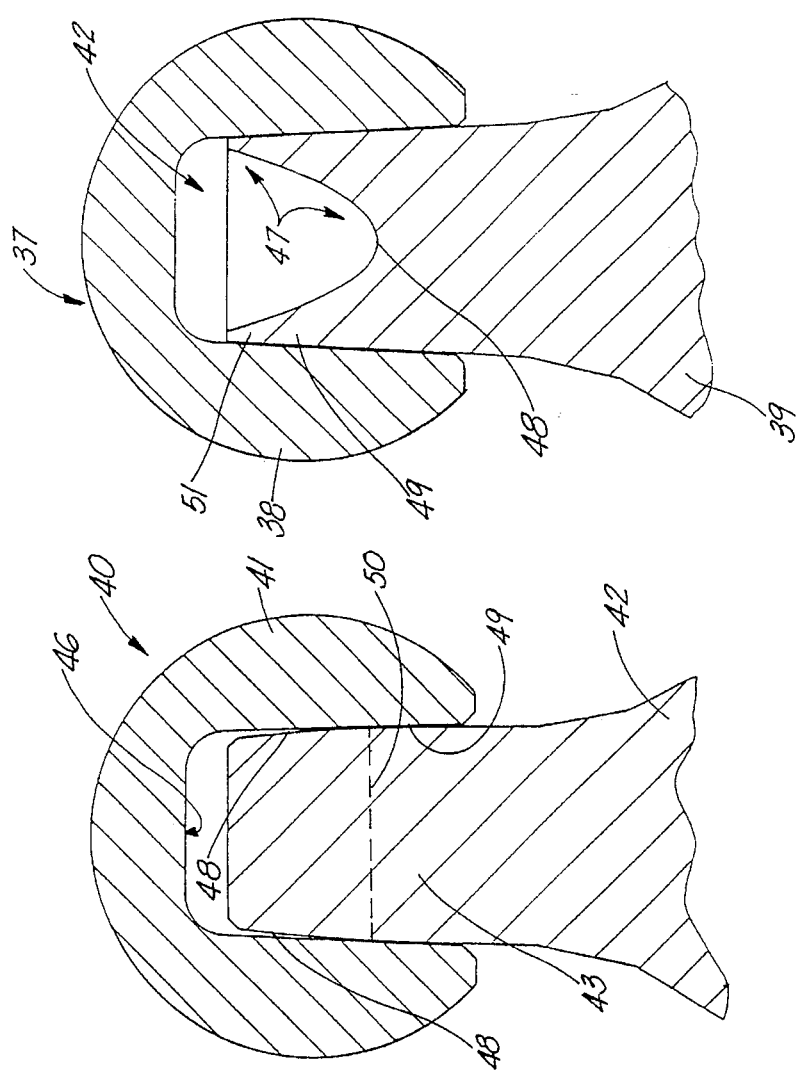

ORTHOPEDIC PROSTHESIS APPARATUS WITH IMPROVED TAPER LOCKING CONNECTION

BACKGROUND OF THE INVENTION

1. Field of the Invention

The present invention relates to an orthopedic joint prosthesis such as a hip stem, knee component, shoulder component, intramedullary nail or the like and more particularly relates to an improved taper lock connection apparatus for joining two prosthetic parts (such as for example the head and stem of a hip implant) wherein stress is reduced by removing material from either the end or the internal circumferential plane of the male taper component, thereby making the male taper component more flexible without an appreciable reduction in structural integrity.

2. General Background

It is known in the art to form a connection between two orthopedic prosthetic components using a morse taper or taper lock connection. One of the most common examples of such a connection is the neck of a hip stem that forms a connection with a correspondingly shaped socket in the ball of the femoral head component typically called the femoral head.

A hip stem neck is often frustroconically shaped and the femoral head of the prosthesis provides a corresponding frustroconical socket for receiving the neck of the hip stem. An example of such a frustroconical neck and its frustroconical socket for a hip stem and ball can be seen in the Fallin U.S. Pat. No. 5,108,452 entitled "Modular Hip Prosthesis" issued Apr. 28, 1992, incorporated herein by reference.

Morse taper or taper lock constructs have also been used for connecting knee components, shoulder components, and intramedullary nail members.

An example of an intramedullary nail with a conical male portion and an axially threaded bore formed in the proximal end of the base portion as seen in U.S. Pat. No. 5,122,141.

Extraction holes are sometimes used in taper designs to provide an attachment point for surgical removal of an implant. This feature can be seen for example in the Genesis Knee System manufactured and sold by Smith and Nephew Richards of Memphis, Tenn., assignee of the present application. In the Genesis Knee System, and attachment point for surgical removal of the implant is provided on male tapers of the tibial stem extension. An extraction hole typically has a thread pattern in the hole to accommodate a male threaded hammer to assist in surgical removal.

Tapered sleeves have been used for attachment to the frustroconical neck of a hip implant. These tapered sleeves provide a threaded hole to facilitate sleeve removal. Such tapered sleeves have been sold for years by Smith & Nephew Richards, assignee of the present application.

Many issued patents show taper lock or wedge lock connections between orthopedic implants. A recent patent is U.S. Pat. No. 5,246,462 issued to K. Bekki et al. and entitled "Insert for Identifying and Implantable Ceramic Joint Head". An object of this patent is to provide an implantable ceramic head which can be readily marked without a reduction in the strength of the ceramic. In the artificial ceramic joint head of the '462 patent, a recess is provided into which the stem is inserted. An insert with a marking is provided on the bottom of the recess. The connection between the stem and joint head is a male conical taper on the femoral stem and a correspondingly shaped socket on the femoral head.

U.S. Pat. No. 5,181,929 entitled "Femoral Prosthesis Employing a Small Ceramic Ball" discloses a metal rod having a male frustroconical end portion and a femoral head, or ceramic ball having a frustroconical blind recess, assembled by means of a conical sleeve fitment. The ceramic ball is formed of a material having an improved flexion breakage modulus and an improved elasticity modulus.

U.S. Pat. No. 5,122,141 issued to Simpson et al. discloses an intramedullary nail system and method for providing the capability of creating intramedullary nails of any desired length by a combination of a small number of base nail members adapted to be joined at any one of a variety of hollow extension nail members. Any selected extension nail member in order to prevent axial separation of the members. Additionally, each extension nail member is provided with transverse openings adapted to receive a bone screw to secure the intramedullary nail member is infinitely rotationally adjustable about fixation of the extension member with any desired degree of anteversion prior to final assembly of the base nail member with the extension nail member.

U.S. Pat. No. 4,964,869 discloses an assembly of a ceramic head fixed to a rod which assembly is a component of hip prosthesis that has improved distribution of stress transferred from the rod to the ceramic head. The ceramic head includes a blind recess, generally in the shaped of a truncated cone, and to which the male end of the rod is nested, in which this nesting together is provided without play between the ceramic head and the end of the rod in only a portion of the depth of the recess, while in the remaining portion of the recess there is no contact between the ceramic head and the end of the rod.

The Averill et al. U.S. Pat. No. 4,921,500 discloses an adaptor that is interposed between a socket and a ceramic femoral head component and a post on a femoral stem component in the femoral stem of a prosthetic hip joint to enable use of a taper within the socket which is steeper than the taper on the post as to reduce hoop stresses in the ceramic femoral head component while at the same time as accomplishing securement of the ceramic femoral head component upon the post of the existing femoral stem component.

The metal male joint part of a hip prosthesis has a taper which is less than that of the cavity of an oxide ceramic female joint part in U.S. Pat. U.S. 4,058,856 entitled "Joint Endoprosthesis". In addition, the surface of the male part has a resistance of defamation which is less than that of the core male part. The cone angle of the female cavity and the cone angle of the male joint part differ.

U.S. Pat. No. 5,080,685 discloses a hip prosthesis that uses a wedge lock taper between the femoral head and the hip stem neck or trunion.

U.S. Pat. No. 4,268,919 discloses a joint endoprosthesis that includes a pivot body with a radially extending hole, a pin press fit in the hole, a recess extending into the pin from its end of the hole, wedging means for spreading the pin from its end in the hole, wedging means for spreading the pin end in the hole in the body to securely hold the pin. U.S. Pat. No. 4,198,711 entitled "Joint Endoprosthesis" discloses a prosthesis that includes a pivot body with a radially extending hole, a pin press fit in the hole, a recess extending into the pin and its end in the hole wedging means for spreading the pin from its end in the hole, wedging means for spreading the pin end in the hole in the body to securely hold the pin.

Zeibig et al. U.S. Pat. No. 4,170,794 discloses a bone joint endoprosthesis that comprises a spherical body of the joint with a hole in it for receiving a shaft spigot, a shaft is embedded in the bone, the shaft has a spigot which is received in the hole, a spreader, comprised of a material that swells when it is wetted, is rapped over the spigot in the hole or is inside the spigot and the spreader expands radially in the hole or inside the spigot to secure the joint, shaping and profiling of the spigot in the wall of the hole for effective retention of the spreader are disclosed.

An artificial head assembly for a human femur is disclosed is U.S. Pat. No. 4,012,795 issued to Doore et al. The apparatus consists of a head portion proper and a metal pin. The head portion is a centered ceramic ball having a polished contact face of convex, spherical curvature and a blind bore tapering conically inward toward the contact face. The pin is shaped for insertion of one end into the hollow stump of the femur, the other end tapering conically at the same apex angle as the bore in the ball. A knurling of the conical face of the pin reduces compressive strength of the pin surface to less than tensile strength of the ball so that the assembled head and pin can be sterilized without cracking the ceramic head portion because of difference in coefficients of thermal expansion between the metal and the ceramic material.

SUMMARY OF THE INVENTION

High stress can be generated at the taper locking connection between interlocking orthopedic implant members. Thus it is desirable to reduce the stress in a taper construct. The present invention is directed to an apparatus and method of reducing stress in a taper/head construct based on a removing of material within the end or the internal circumferential plane of the male taper member. This concept is designed to make the taper junction more flexible without an appreciable reduction in structural integrity.

The concept of stress reduction is accomplished by removal of material either at the end or in the circumferential plane of the taper normal to the axis of the taper. A flexible taper construct will decrease the peak contact stress, decrease the hoop stress in the female member and increase the contact area.

The apparatus of the present invention can be applied to hip stem/hip head tapers, hip stem extension tapers, knee component stem extension tapers, shoulder component tapers, and intramedullary nail tapers. In a hip implant, the apparatus of the present invention can be used to reduce the stress in the femoral head. This allows for smaller diameter ceramic heads. It would also provide for a greater factor of safety in current head designs.

In knee implants, a reduction in stress is an advantage gained by using the apparatus of the present invention.

The present invention provides an improved orthopedic joint prosthesis apparatus that includes a prosthesis body having a male connecting portion with a generally frustroconically shaped outer surface. The male connecting portion provides a distal end with a layer generally circular end face and a proximal end with a smaller generally circular end face.

In the preferred embodiment, an annular groove is located on the cirular face of the prosthesis. The annular groove provides for more uniform stress distribution between the proximal and distal end portions, and increasing flexibility of the projecting connecting portion.

The void can also take the form of a socket that communicates with the proximal end face of the projecting connecting portion. The socket can have a closed end portion that is preferably parabolically shaped.

In one embodiment, the void space is in the form of a plurality of sockets that communicate with the proximal end face of the projecting connecting portion.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 4 is a sectional elevational view of the first, preferred embodiment of the apparatus of the present invention;

FIG. 5 is a sectional view of the second embodiment of the apparatus of the present invention;

FIG. 6 is a sectional view of the third embodiment of the apparatus of the present invention;

DETAILED DESCRIPTION OF THE PREFERRED EMBODIMENT

Figure 1:
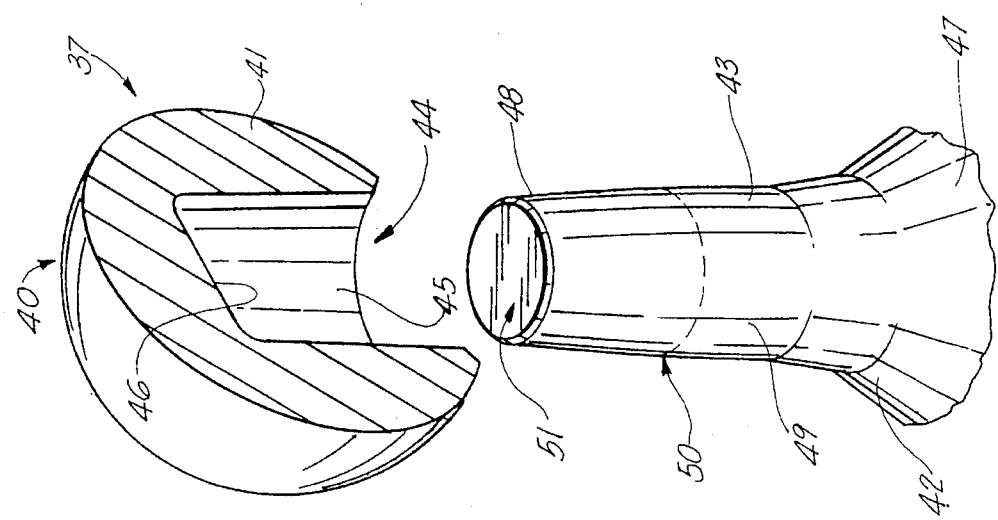
FIG. 1 is a perspective view of the first, preferred embodiment of the apparatus of the present invention.

FIGS. 1 and 4 illustrate the preferred embodiment of the apparatus of the present invention designated generally by the numeral 10. Orthopedic implant 10 includes an acetabular ball 11 that attaches to hip stem 12. However, other types of orthopedic implants could be connected together using the improved taper lock of the present invention such as for example for knee implants, shoulder implants, intramedullary nails, and the like. Acetabular ball 11 provides a hemispherical outer surface 13 for connection to an acetabular cup component for example. Hip stem 12 has a neck section 14 that forms a connection with socket 15 of ball 11. Socket 15 has a frustroconical side wall 16 and a circular end wall 17.

Neck section 14 provides a circular end surface 18 and a frustroconical surface 19. Hip stem 12 can be thickened at 24 as shown for example in the DeMane U.S. Pat. No. 5,108,452, incorporated herein by reference. Neck section 14 provides a circular end surface 18 with annular groove 20 formed thereon as shown. Annular groove 20 has a closed lower end 22. Groove 20 defines a thin annular shoulder 21 with the frustroconical outer surface 19 of neck 14. This small annular shoulder 21 can flex to reduce stresses from the vicinity of the groove 20. As an alternate construction, a plurality of small circumferentially spaced holes could be used in place of groove 20. The holes could be placed in a circular path that similarly tracks the circular as pathway as defined by annular groove 20.

Figure 2:
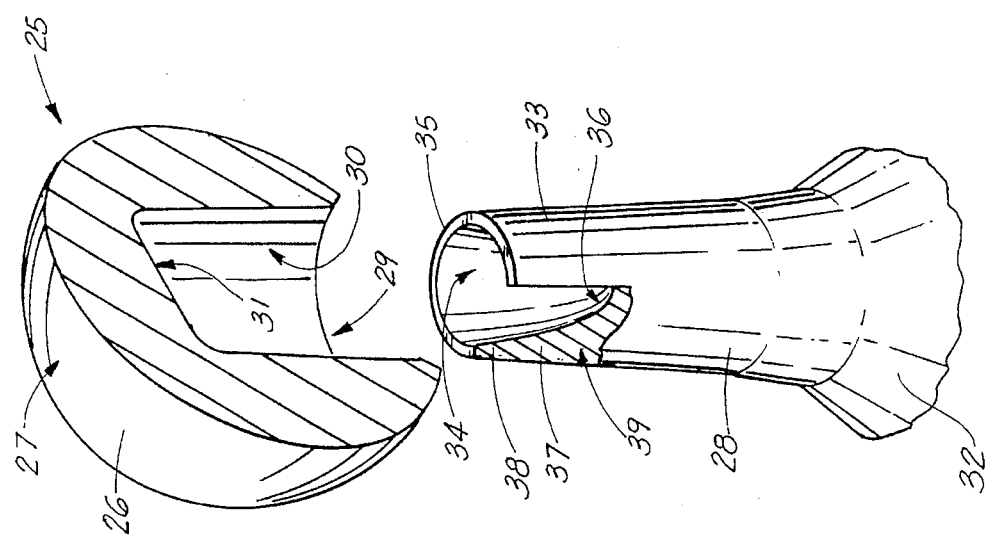
FIG. 2 is perspective view of a second embodiment of the apparatus of the present invention.

In FIGS. 2 and 5, a second embodiment of the apparatus of the present invention is designated generally by the numeral 25. In the embodiment of FIG. 2, orthopedic prosthesis 25 includes acetabular ball 26 having hemispherical outer surface 27 and socket 29 for connecting to neck section 28 of a hip prosthesis for example. Socket 29 provides a frustroconical side wall 30 and an circular end wall 31. Neck section 28 has an outer surface 33 that is frustroconically shaped. In the embodiment of FIG. 2, socket 34 extends from annular shoulder 35 a partial distance along neck section 28 as shown. Socket 34 gradually tapers until it reaches closed end portion 36. Socket 34 thus forms an annular wall 37 that begins at a thinner wall portion 38 adjacent to annular shoulder 35 and gradually thickens to a thicker wall portion 39 adjacent closed end portion 36. The socket 34 defines a gradually thickening annular wall 37 that can be designed to have a desired flexibility for reducing stresses formed between neck section 28 and ball 26 upon assembly. A thickened portion 24 can be provided to hip implant as with the embodiment of FIG. 1.

Figure 3:
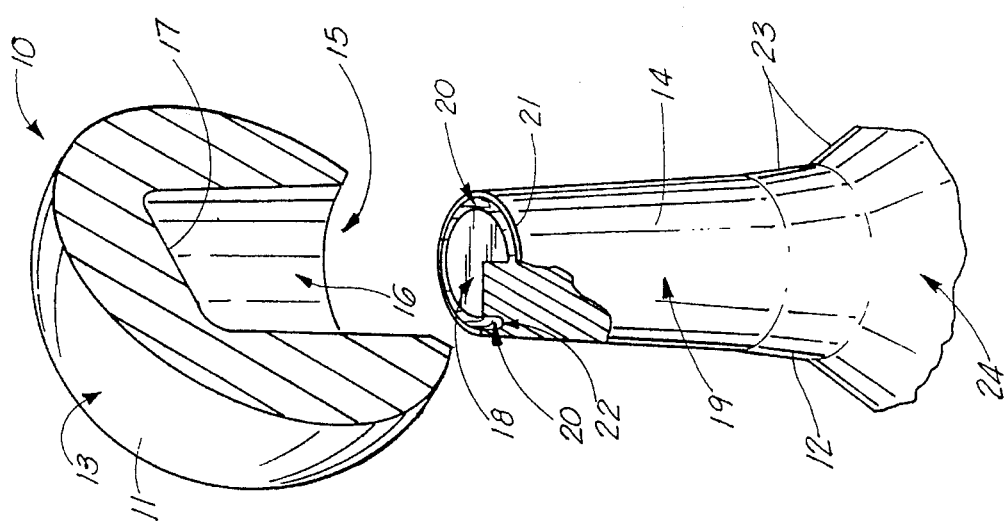
FIG. 3 is a perspective view of a third embodiment of the apparatus of the present invention.

FIGS. 3 and 6 illustrate a third embodiment of the apparatus of the present invention designated generally by the numeral 40. Orthopedic implant 40 includes an acetabular ball 41 and hip stem 42. Hip stem 42 provides neck section 43. Neck section 43 forms a connection with socket 44, preferably a taper lock connection or morse taper connection. Socket 44 is defined by frustroconical sidewall 45 and circular end wall 46.

Hip stem 42 includes a thickened section 47 below neck section 43. The neck section 43 includes a pair of frustroconical sections 48, 49. The frustroconical sections 48, 49 are separated by an annular transition line 50 as shown in FIGS. 3 and 6. The taper on section 48 is greater than than the taper on section 49, as can be seen in FIG. 6. Neck section 43 also includes a circular end 51 as shown in FIG. 3.

In FIGS. 3 and 6, the transition between frustroconical section 48 and frustroconical section 39 is schematically indicated by the dotted line 50. As with the preferred embodiment, a thickened portion 47 can be provided to the hip stem 42.

Figure 8B:
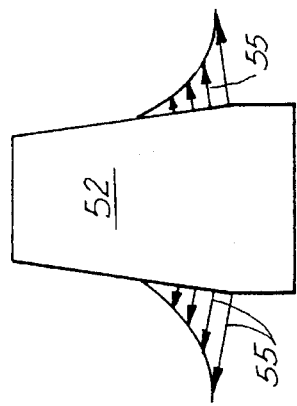
FIGS. 8A–8C are schematic view illustrating pressure distribution for the connection between head and taper that is generated in typical prior art femoral head and hip implant prosthetic devices FIG. 8A for proximal contact, FIG. 8B for distal contact, and FIG. 8C for conforming contact.
Figure 8A:
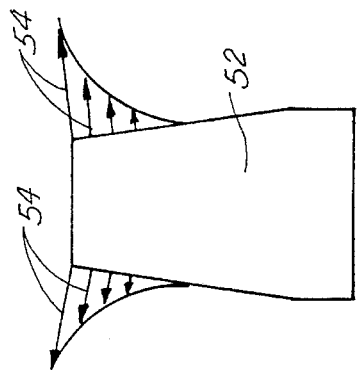
Figure 7:
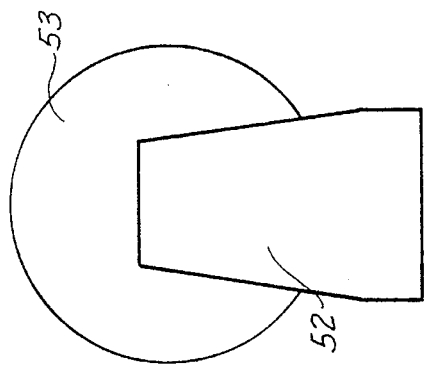
FIG. 7 is a sectional view of a typical prior art tapered junction of a femoral head and hip implant.
Figure 8C:
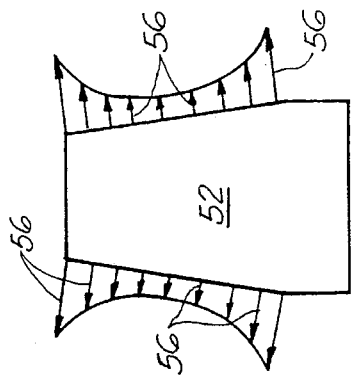

FIG. 7 shows a typical prior art morse taper connection between a neck 52 of a hip stem and an acetabular ball 53. FIGS. 8A–8C and 9–10 show various graphical representations of stress distributions for a prior art type taper lock connection and for the embodiments of the present invention as shown in FIGS. 1–6. FIGS. 8A, 8B, and 8C show various stress distributions that are experienced by the prior art type ball 53 and neck 52 hip prosthesis of FIG. 7. In FIG. 8A, stress distribution arrows 54 are shown at the proximal end of neck 52. In FIG. 8B stress distribution arrows 55 show schematically a stress distribution at the distal end of neck 52. In FIG. 8C, stress distribution arrow 56 show a typical stress distribution for the prior art prosthesis of FIG. 7, wherein stress distribution is at the proximal and distal ends of the neck 52.

Figure 10:
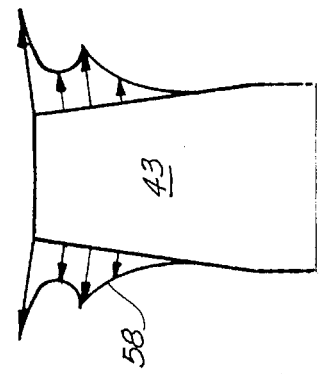
FIG. 10 is a stress distribution illustration for the embodiment of FIG. 3.
Figure 9:
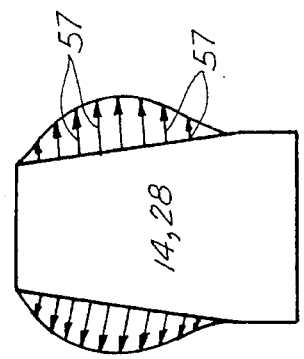
FIG. 9 is a schematic view illustrating a stress distribution generated by each of the embodiments of the apparatus of the present invention shown in FIGS. 1 and 2.

FIG. 9 illustrates a stress distribution for the embodiments of FIGS. 1 and 2, with stress distribution arrows 57. FIG. 10 illustrates a stress distribution using arrows 58 for the preferred embodiment of FIG. 3.

The following table lists the parts numbers and parts descriptions as used herein and in the drawings attached hereto.

PARTS LIST

| Part Number | Description |
| --- | --- |
| 10 | orthopedic implant |
| 11 | acetabular ball |
| 12 | hip stem |
| 13 | spherical outer surface |
| 14 | neck section |
| 15 | socket |
| 16 | frustroconical side wall |
| 17 | circular end wall |
| 18 | circular surface |
| 19 | frustroconical outer surface |
| 20 | annular groove |
| 21 | annular shoulder |
| 22 | closed end |
| 23 | hip prothesis |
| 24 | thickened portion |
| 25 | orthopedic prosthesis |
| 26 | acetabular ball |
| 27 | spherical outer surface |
| 28 | neck section |
| 29 | socket |
| 30 | frustroconical side wall |
| 31 | circular end wall |
| 32 | thickened section |
| 33 | frustroconical surface |
| 34 | socket |
| 35 | annular shoulder |
| 36 | closed end |
| 37 | wall |
| 38 | thin portion |
| 39 | thick portion |
| 40 | orthopedic implant |
| 41 | acetabular ball |
| 42 | hip stem |
| 43 | neck section |
| 44 | socket |
| 45 | frustroconical side wall |
| 46 | circular end wall |
| 47 | thickened section |
| 48 | frustroconical section |
| 49 | frustroconical section |
| 50 | transition line |
| 51 | circular end |
| 52 | neck |
| 53 | ball |
| 54 | arrows |
| 55 | arrows |
| 56 | arrows |
| 57 | arrows |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An orthopedic joint prosthesis comprising:

a) a prosthesis body that includes a pair of connectable components, each having a connecting portion with a generally frustroconically shaped connecting surface, a first of the components having a projecting connecting portion, and a second of the components having a socket connecting portion;

b) the projecting connecting portion having a central longitudinal axis, a distal end portion and a proximal end, the proximal end having a generally circular end face;

c) a groove communicating with the proximal circular face;

d) wherein the groove is radially spaced from and circumferentially extending about the projecting portion axis, said groove enabling a distribution of stress between said proximal and distal end portions;

e) wherein the groove extends from the circular end face a partial distance between the proximal and distal ends; and f) the projecting connecting portion frustroconically-shaped connecting surface extending farther from the end face than the groove.

2. The apparatus of claim 1 wherein the void space is a circumferential annular bevel at the proximal end of the projecting connecting portion.

3. The apparatus of claim 1 wherein the groove is an annular groove that communicates with the distal end of the first component.

4. The apparatus of claim 1 wherein the first component has a generally flat proximal surface.

5. The apparatus of claim 1 wherein the second component is a spherically shaped member.

6. The apparatus of claim 1 wherein the first component is a frustroconically-shaped member in between its proximal and distal end portions.

7. The apparatus of claim 1 wherein the second component is an acetabular ball prosthesis.

8. The apparatus of claim 1 wherein the first component is a hip prosthesis.

* * * * *